United States Patent
Qian

(10) Patent No.: US 9,068,214 B2
(45) Date of Patent: Jun. 30, 2015

(54) METHOD FOR PREPARING (R)-PRAZIQUANTEL

(71) Applicant: TONGLI BIOMEDICAL CO., LTD, Suzhou, Jiangsu Province (CN)

(72) Inventor: Mingxin Qian, Suzhou (CN)

(73) Assignee: Tongli Biomedical Co., Ltd, Suzhou, Jiangsu Province (CN)

( * ) Notice: Subject to any disclaimer, the term of this patent is extended or adjusted under 35 U.S.C. 154(b) by 0 days.

(21) Appl. No.: 14/471,841

(22) Filed: Aug. 28, 2014

(65) Prior Publication Data

US 2014/0370556 A1   Dec. 18, 2014

Related U.S. Application Data

(63) Continuation of application No. PCT/CN2013/072022, filed on Feb. 28, 2013.

(30) Foreign Application Priority Data

Feb. 28, 2012  (CN) .......................... 201210046090.9

(51) Int. Cl.

| | |
|---|---|
| C07D 471/08 | (2006.01) |
| C12P 41/00 | (2006.01) |
| C07D 471/04 | (2006.01) |
| C07D 211/60 | (2006.01) |
| C07B 53/00 | (2006.01) |
| C07D 217/14 | (2006.01) |
| C07D 217/16 | (2006.01) |
| C07D 217/26 | (2006.01) |
| C12P 17/12 | (2006.01) |
| C12P 17/18 | (2006.01) |

(52) U.S. Cl.
CPC ............... *C12P 41/00* (2013.01); *C07D 471/04* (2013.01); *C07D 211/60* (2013.01); *C07B 53/00* (2013.01); *C07D 217/14* (2013.01); *C07D 217/16* (2013.01); *C07D 217/26* (2013.01); *C12P 17/12* (2013.01); *C12P 41/004* (2013.01); *C12P 17/182* (2013.01)

(58) Field of Classification Search
None
See application file for complete search history.

(56) References Cited

U.S. PATENT DOCUMENTS 4,497,952 A    2/1985  Kim et al.

FOREIGN PATENT DOCUMENTS

| CN | 101100684 | 1/2008 |
|---|---|---|
| CN | 102260721 | 11/2011 |

OTHER PUBLICATIONS

Roszkowski, P., et al., Enantioselective synthesis of (R)-(-)-praziquantel (PZQ), Tetrahedron: Asymmetry, vol. 17, No. 9, 2006, pp. 1415-1419, see p. 1416.

Ma, Chen, et al., Total synthesis of (-)-praziquantel: an anthelmintic drug, Journal of Chemical Research, 2004, No. 3, pp. 186-197, see 186.

*Primary Examiner* — Zinna Northington Davis

(74) *Attorney, Agent, or Firm* — Stites & Harbison PLLC; Cong Ding

(57) ABSTRACT

The invention relates to a new method for preparing (R)-praziquantel. In the invention, by taking advantage of the high stereo selectivity, site selectivity and region selectivity of an enzyme, an intermediate of a pure optical and chiral (R)-praziquantel are obtained by means of the dynamic kinetic resolution of an enantiomer from the synthesized racemate or derivatives thereof, and the (R)-praziquantel is obtained by using various conventional and mature organic chemical reactions with higher yield. The method of the invention has the potential advantages of easily available raw materials, low cost, environmentally safer process and convenience for large-scale production. Also, the purity of the end product can be more than 98%. By adopting the invention, the quality of the product is improved and a basis for developing high quality of active pharmaceutical ingredients and formulations is established, and thus the pending industrial problem of purifying praziquantel over 30 years becomes solvable.

15 Claims, No Drawings

METHOD FOR PREPARING (R)-PRAZIQUANTEL

CROSS-REFERENCES TO RELATED APPLICATIONS

This application is a continuation application of PCT Patent Application No. PCT/CN2013/072022, filed Feb. 28, 2013, which claims priority to CN201210046090.9 filed Feb. 28, 2012; the disclosures of each is hereby incorporated by reference in its entirety and for all purposes.

FIELD OF THE INVENTION

The present invention relates to a method for preparing (R)-praziquantel.

DESCRIPTION OF THE RELATED ART

Praziquantel is a broad spectrum antiparasitic drug and a racemic mixture. It has a wide anthelmintic activity on *Schistosoma japonica*, *Schistosoma haematobium*, *Schistosoma mansoni* and the like. Furthermore, praziquantel also has activity against *Paragonimus westermani*, *Clonorchis sinensis*, *Echinococcus*, *Cysticercus*, *Sparganosis mansoni*, *Fasciolopsis*, *Cestode* and the like. In addition, praziquantel has the advantages of high efficacy, short course of treatment, small dose, fast metabolism, low toxicity and convenient oral administration. Thus, the discovery of praziquantel is a major breakthrough on chemotherapy of parasitic diseases, and praziquantel has become a drug of choice for treatment of various helminthiases.

Praziquantel was firstly synthesized by Seubert at al. in 1975, and was developed as a drug by the two pharmaceuticals companies, Merck KGaA and Bayer AG. In 1980, praziquantel was firstly on the market under the trade name of Cesol, and now it has been used extensively in the world. Besides for human therapy, praziquantel is also broadly used for treatment of parasitic diseases in animals including poultries or the like. However, in the conventional manufacture processes for preparing praziquantel, usually some toxic and harmful chemicals, such as potassium cyanide and cyclohexanecarboxylic acid chloride, are needed and a longer process route) and a relative harsh reaction condition are used (see the following scheme).

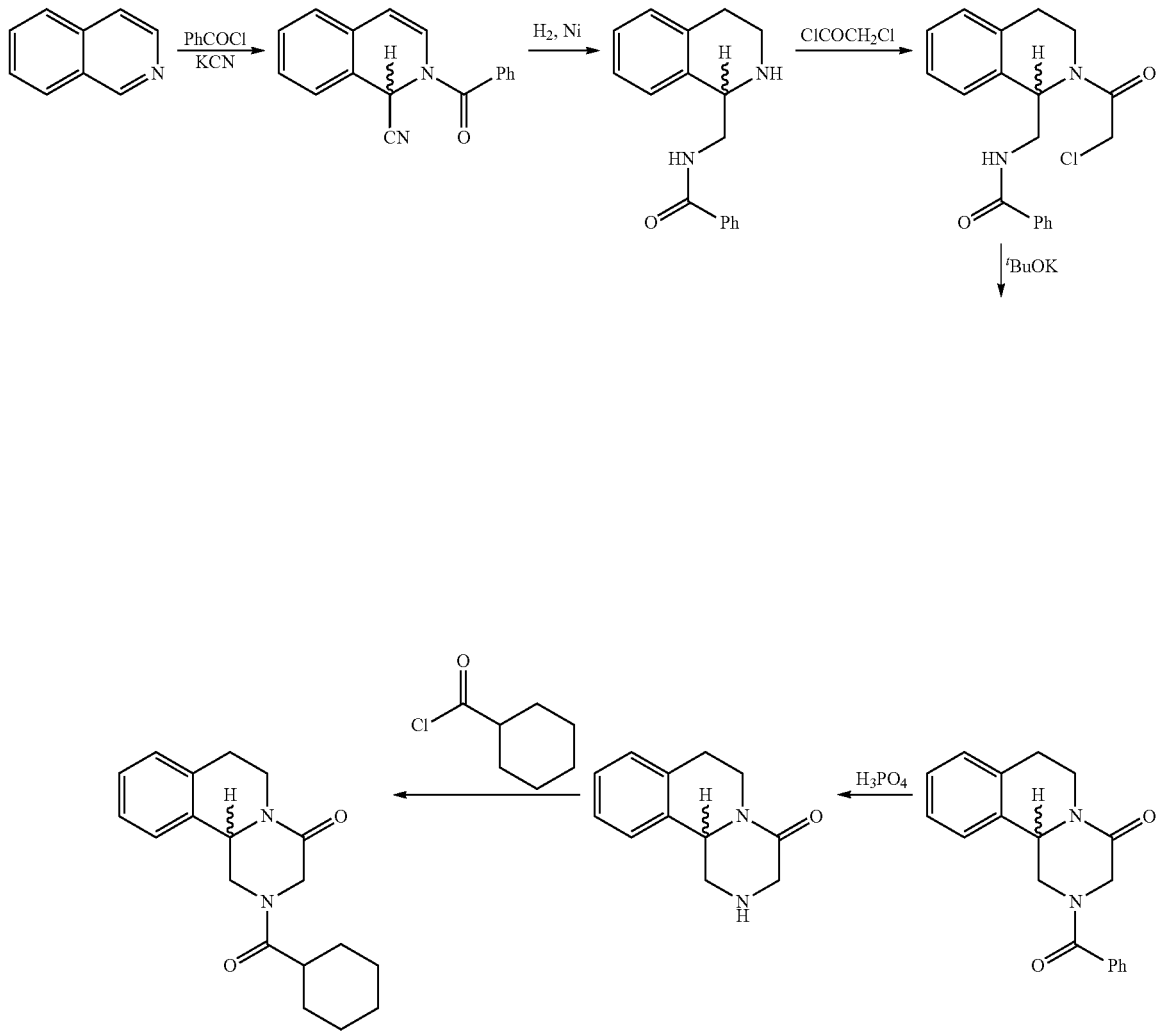

3

In early 1980, two optical isomers, (R)-praziquantel and (S)-praziquantel, are obtained from synthesized praziquantel using resolution by some researchers. It has been found from the pre-clinical studies and preliminary clinical trials that: (R)-praziquantel is an active isomer in praziquantel while (S)-praziquantel is an inactive and even harmful component. At the same dosage, (R)-praziquantel has a better clinical efficacy than praziquantel. Alternatively, it has been desired and proposed to develop (R)-praziquantel by the World Health Organization. However, over the years the technical problem of low yield on synthesizing (R)-praziquantel is still unsolvable.

SUMMARY OF THE INVENTION

A technical problem to be solved by the invention is to provide a method for preparing (R)-praziquantel with an environmentally safer process and a high yield. In order to solve the above technical problem, in one aspect, the invention provides a method for preparing (R)-praziquantel using the following reaction scheme:

4 to obtain a pure optical (R)-tetrahydroisoquinoline formamide having the structure of compound 14.

Preferably, the lipase is selected from one or more microbial lipases derived from the group consisting of *Aspergillus niger, Candida rugosa (Candida cylindracea), Rhizomucor miehei, Candida Antarctica, Pseudomonas cepacia, Pseudomonas fluorescens, Thermomyces lanuginose, Bacillus subtilis, Fusarium solani pisi, Alcaligenes* sp, *Rhizopus niveus, Mucor javanicus* and *Rhizopus oryzae*, and the lipases derived from *Thermomyces lanuginose, Fusarium solani pisi, Bacillus subtilis, Pseudomonas cepacia* and *Pseudomonas fluorescens*, and any combination thereof.

Preferably, R is selected from the group consisting of methyl, ethyl, isopropyl, tert-butyl and the like.

More preferably, the racemic compound 3e is reacted with the lipase, an ammonia gas and/or an ammonia source which can be decomposed to produce ammonia gas in a solvent in the presence of an ionic liquid at 0-50° C., to produce compound 14.

More preferably, the solvent is selected from the group consisting of tertiary butanol, diisopropyl ether ester, dioxane, tetrahydrofuran, isopropanol, methyl tert-butyl ether and any combination thereof.

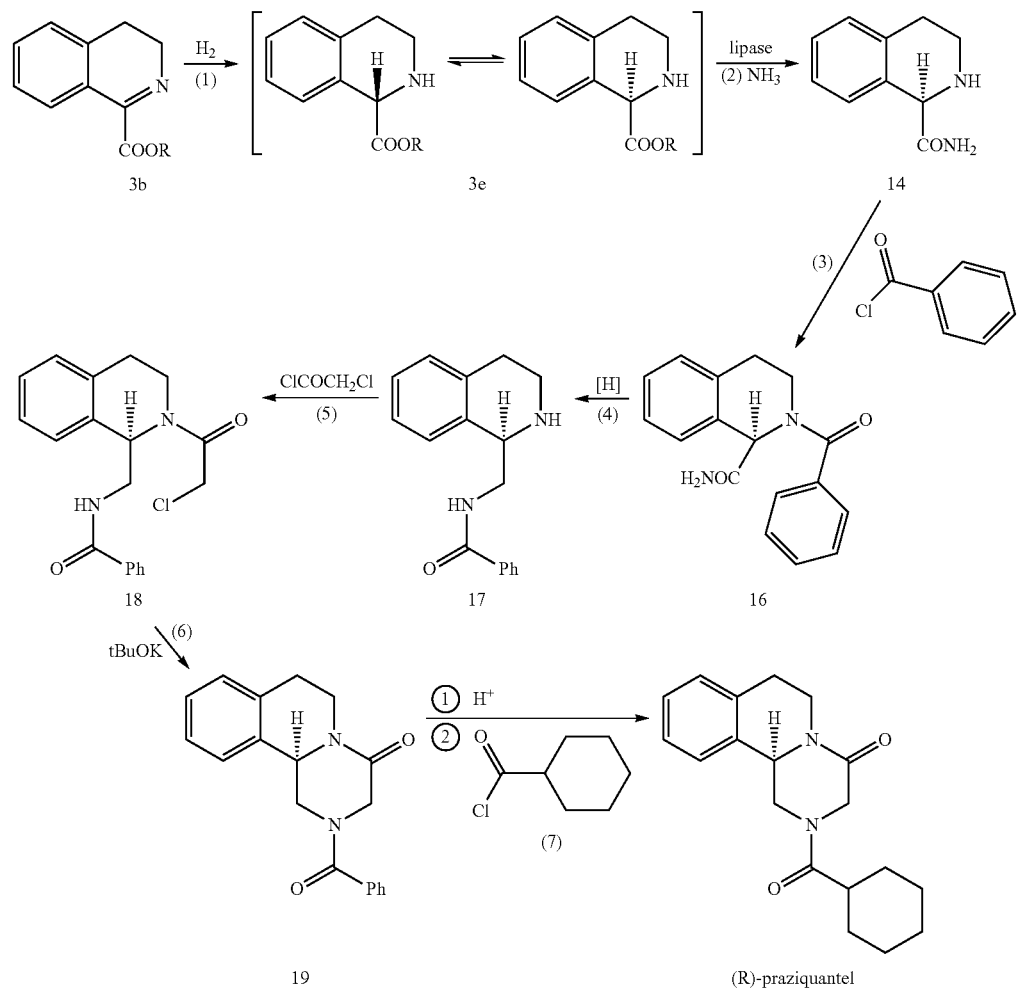

wherein
R represents alkyl; and
wherein the lipase stereo-selectively ammonolyzes a (R)-tetrahydroisoquinoline formate of the racemic compound 3e More preferably, the ionic liquid is selected from the group consisting of 1-n-butyl-3-methylimidazolium tetrafluoroborate, 1-n-butyl-3-methylimidazolium hexafluorophosphate, 1-n-butyl-3-methylimidazolium bis[(trifluoromethyl)sulfonyl]imide and 1-n-butyl-pyridinium hexafluorophosphate.

Still more preferably, the ammonia source is selected from one or more of ammonia gas, ammonium carbamate, ammonium formate, acetic ammonia and ammonia chloride.

Still more preferably, the reaction of step (2) is performed in the presence of an organic base selected from the group consisting of triethylamine, imidazole, pyridine, tetrabutyl ammonium hydroxide and any combination thereof.

Preferably, the reaction temperature is 20-50° C.

In a specific embodiment, the step (2) is implemented as follows: the racemic compound 3e, an ionic liquid, a solvent and an optional organic base are added to a sealed reactor, and an ammonia source is added and stirred evenly; then a lipase is added to start the reaction in a constant temperature vibrator with HPLC monitoring the reaction; and the reaction is ended when the reaction conversion is more than 99%, subsequently the lipase is recycled by filtering for use in a next batch reaction, and the filtrate is post-processed to get the (R)-praziquantel.

The post-processing comprises the steps of:
adding dropwise hydrochloric acid to the filtrate at 20-25° C.;
standing and layering the resulting solution, such that an upper layer is formed by the ionic liquid and the solvent, and the other components containing the compound 14 are in a lower layer of water phase;
separating the upper layer and washing it with saturated sodium bicarbonate and saturated salt water respectively, and incorporating the washing liquid to the lower layer of water phase; and
neutralizing the water phase to neutrality with saturated sodium bicarbonate, and extracting the solution with ethyl acetate, and drying over anhydrous sodium sulfate and evaporating off the solvent to get the residue, and recrystallizing the residue with ethanol to get the white solid of compound 14.

More preferably,
in the step (1), the compound 3b is reacted with $H_2$ at 60-70° C. in the presence of a Pd/C catalyst, and when the reaction is ended the catalyst is recycled by filtering, and the filtrate is concentrated under reduced pressure to get the racemic compound 3e.

the step (3) is implemented as follows: the compound 14, triethylamine and dichloromethane are added to a reactor and cooled to 0-2° C. in ice bath, and benzoyl chloride is added dropwise under stirring at 0-2° C.; when the addition is completed, the reaction mixture is stirred at 20-25° C. for 6-8 hours with HPLC monitoring the reaction, subsequently when the reaction is completed, the reaction is quenched with water and stirred for further 30-40 mins; finally the organic phase layer is separated, washed, dried, and concentrated under reduced pressure, and the residue is recrystallized with ethanol to get compound 16;

in the step (4), the compound 16, an anhydrous methanol and a ruthenium catalyst Ru/C are added to a sealed reactor, and $H_2$ is introduced continuously to the reactor after the air in the reactor has been replaced with $H_2$, then the mixture is heated to 90-95° C. and stirred for 16-18 hours until the analysis indicating the completion of the reaction; the catalyst is recycled by filtering and the filtrate is concentrated under reduced pressure to get the residue, finally the residue is recrystallized with the mixed solvent of ethanol and n-hexane in a volume ratio of 1:2-4 to get light yellow solid of compound 17.

the step (5) is implemented as follows: the compound 17, an organic solvent and a solution of a base are added to a reactor and stirred evenly, and chloroacetylchloride is added dropwise, when the addition is completed, the mixture is stirred at room temperature for 3-4 hours until HPLC analysis indicating the completion of the reaction, wherein the resulting reaction mixture can be directly used in a next reaction.

the step (6) is implemented as follows: benzyl-triethyl ammonium chloride is added to the reaction mixture of step (5), and heated to 75-85° C. to perform the reaction for 1-2 hours until HPLC analysis indicating the completion of the reaction; the insoluble is filtered out, and the layer of organic solvent is washed, dried and concentrated under reduced pressure to get the crude product, finally the crude product is recrystallized with anhydrous ethanol to get compound 19.

the step (7) is divided into two sub-steps:
a. the intermediate R-(-)-praziquantel amine is prepared from compound 19 in the presence of phosphoric acid or hydrochloric acid; and

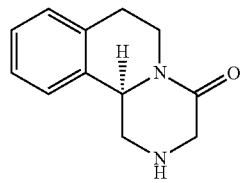

R-(-)-praziquantel amine b. the intermediate R-(-)-praziquantel amine is reacted with cyclohexane formyl chloride in a solvent in the presence of triethylamine at 20-25° C. to get (R)-praziquantel.

The invention also provides a method for preparing an intermediate of (R)-praziquantel, wherein the racemic tetrahydroisoquinoline formate of general formula 3e is reacted with a lipase, an ammonia gas and/or an ammonia source which can be decomposed to produce ammonia gas in a solvent in the presence of an ionic liquid at 0-50° C., to produce the intermediate of (R)-praziquantel, and the reaction scheme is provided as follows:

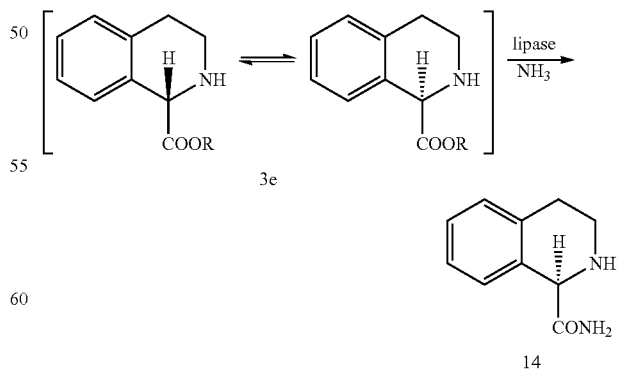

R represents alkyl; and
the lipase stereo-selectively ammonolyzes a (R)-tetrahydroisoquinoline formate of the racemic compound 3e to obtain a pure optical intermediate of (R)-praziquantel, (R)-tetrahydroisoquinoline formamide having the structure of compound 14.

This method can be specifically implemented as follows: the racemic compound 3e, an ionic liquid, a solvent and an optional organic base are added to a sealed reactor, and the ammonia source is added or ammonia gas is introduced and stirred evenly; and a lipase is added to start the reaction in a constant temperature vibrator with HPLC monitoring the reaction; the reaction is ended when the reaction conversion is more than 99%, and the lipase is recycled by filtering for use in a next batch reaction. Hydrochloric acid is dropwise added to the filtrate at 20-25° C.; and an upper layer is formed by the ionic liquid and solvent, and the other components containing the intermediate of (R)-praziquantel is in the lower layer of water phase after standing and layering of the resulting solution; the upper layer is separated, and washed with saturated sodium bicarbonate and saturated salt water respectively, and the washing liquid is incorporated to the lower layer of water phase; subsequently the water phase is neutralized to neutrality with saturated sodium bicarbonate, and the solution is extracted with ethyl acetate, dried over anhydrous sodium sulfate and concentrated to get the residue, and the residue is recrystallized with ethanol to get the white solid of the intermediate of (R)-praziquantel.

By adopting the above technical solutions, as compared with the prior art the invention has the following advantages:

The invention is applicable for large-scale industrial production through the synthesis route using bio-enzyme catalysis. In the method of the invention, by taking advantage of the high stereo-selectivity, site selectivity and region selectivity of an enzyme, an intermediate (R)-compound 4 of a pure optical and chiral (R)-praziquantel are obtained by means of the dynamic kinetic resolution of an enantiomer of the synthesized racemate or derivatives thereof. The method of the invention has the potential advantages of mature yet environmentally improved process, easily available raw materials and low cost. Accordingly, the method of the invention is conveniently adoptable for large-scale production of (R)-praziquantel with an improved quality. In the invention, the purity of the product can be more than 98%. These improvements will lay a foundation for further development of high-quality active pharmaceutical ingredients and pharmaceutical formulations, and make the pending industrial problem of separation and purification of high purity of (R)-praziquantel over the past 30 years solvable.

In the invention, the bio-enzyme catalysis is utilized as a core technology to develop a high yield and environmentally safer process for chiral synthesis of (R)-praziquantel. This will pave the way for further preclinical and clinical evaluation, large-scale manufacturing and eventually entering international market of (R)-praziquantel.

DESCRIPTION OF THE PREFERRED EMBODIMENTS

The invention will be further detailedly illustrated in connection with specific embodiments. However, the invention is not limited to the following embodiments.

The lipases used in the embodiments of the invention are described in the following table 1.

TABLE 1

| code | lipase | source (english) | commercial source |
|---|---|---|---|
| L-AK | Lipase AK "AMANO" | Pseudomonas fluorecens | powder, available from Amano company |
| L-AS | Lipase AS "AMANO" | Aspergillus niger | powder, available from Amano company |
| L-AY | Lipase AY "AMANO" | Candida rugosa | powder, available from Amano company |
| L-PS | Lipase PS "AMANO" IM | Pseudomonas cepacia | powder, available from Amano company |
| CALB | IMMOZYME CALB | Candida antarctica | immobilized, available from Sigma company |
| RML | IMMOZYME RML | Rhizomucor miehei | immobilized, available from Sigma company |
| TLL | IMMOZYME TLL | Thermomyces lanuginosa | immobilized, available from Sigma company |
| Novo 51032 | Lipase Novozyme 51032 | Fusarium solani pisi | immobilized, available from Sigma company |
| AULI | IMMOZYME AULI | Bacillus subtilis | immobilized, available from Sigma company |

Embodiment 1

Synthesis of Tetrahydroisoquinoline Formate Using the Following Reaction Scheme

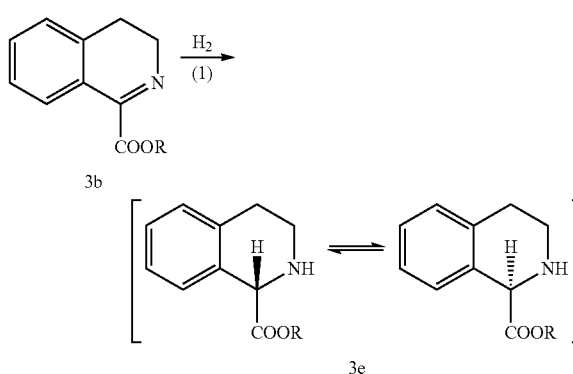

Wherein R represents methyl, ethyl, isopropyl, tert-butyl or p-methoxylphenyl.

Example 1-1 to a sealed vessel dihydro isoquinoline methyl formate (756.8 g, 4 mol), ethanol (7 L) and 10% Pd/c catalyst (60 g) were added, and $H_2$ (3 MPa) was continuously introduced into the vessel after the air in the vessel was replaced with $H_2$, then the reaction mixture was heated to 65° C. and stirred for 24 hours. When analysis indicated the completion of the reaction, the catalyst was recycled by filtering, and the filtrate was concentrated under reduced pressure to get 749.6 g oily compound of tetrahydroisoquinoline methyl formate (hereinafter known as compound 3e-1), and the purity of the compound was 95% and the yield was 98%.

The NMR data of the compound 3e-1 was as follows:

$^1$H NMR (CDCl$_3$, 400 MHz, δ ppm): 1.35 (s, 3H, CH$_3$), 2.03-2.21 (brs, 1H), 2.68-2.74 (m, 2H), 2.98-3.01 (t, J=5.9 Hz, 2H), 4.54 (s, 1H), 7.02-7.40 (m, 4H, ArH).

Example 1-2 to a sealed vessel dihydro isoquinoline ethyl formate (812.9 g, 4 mol), ethanol (7 L) and 10% Pd/c catalyst (60 g) were added, and $H_2$ (3 MPa) was continuously introduced into the vessel after the air in the vessel was replaced with $H_2$, then the reaction mixture was heated to 65° C. and stirred for 24 hours. When analysis indicated the completion of the reaction, the catalyst was recycled by filtering, and the filtrate was concentrated under reduced pressure to get 804.58 g oily compound of tetrahydroisoquinoline ethyl formate (hereinafter known as compound 3e-2), and the purity of the compound was 96% and the yield was 98%.

The NMR data of the compound 3e-2 was as follows:

$^1$H NMR (CDCl$_3$, 400 MHz, δ ppm): 1.28-1.37 (t, 3H, —CH$_2$—CH$_3$), 2.01-2.27 (br s, 1H, NH), 2.78-2.84 (m, 2H, CH$_2$), 3.03-3.33 (m, 2H, CH$_2$), 4.19-4.24 (m, 2H, —CH$_2$—CH$_3$), 4.71 (s, 1H, CH), 7.11-7.35 (m, 4H, ArH).

Example 1-3 to a sealed vessel dihydro isoquinoline isopropyl formate (869.0 g, 4 mol), ethanol (7 L) and 10% Pd/c catalyst (60 g) were added, and $H_2$ (3 MPa) was continuously introduced into the vessel after the air in the vessel was replaced with $H_2$, then the reaction mixture was heated to 65° C. and stirred for 24 hours. When analysis indicated the completion of the reaction, the catalyst was recycled by filtering, and the filtrate was concentrated under reduced pressure to get 914.57 g oily compound of tetrahydroisoquinoline isopropyl formate (hereinafter known as compound 3e-3), and the purity of the compound was 94% and the yield was 98%.

The NMR data of the compound 3e-3 was as follows:

$^1$H NMR(CDCl$_3$, 400 MHz, δ ppm): 1.28-1.35 (t, 3H×2, CH$_3$), 2.03-2.22 (br s, 1H, NH), 2.67-2.69 (m, 2H, CH$_2$), 2.83-2.93 (m, 2H, CH$_2$), 4.31-4.54 (m, 1H, —CH—CH$_3$), 4.74 (s, 1H, CH), 7.02-7.32 (m, 4H, ArH).

Example 1-4 to a sealed vessel dihydro isoquinoline tertbutyl formate (925.2 g, 4 mol), ethanol (7 L) and 10% Pd/c catalyst (60 g) were added, and $H_2$ (3 MPa) was continuously introduced into the vessel after the air in the vessel was replaced with $H_2$, then the reaction mixture is heated to 65° C. and stirred for 24 hours. When analysis indicated the completion of the reaction, the catalyst was recycled by filtering, and the filtrate was concentrated under reduced pressure to get 895.91 g oily compound of tetrahydroisoquinoline tertbutyl formate (hereinafter known as compound 3e-4), and the purity of the compound was 96% and the yield was 96%.

The NMR data of the compound 3e-4 was as follows:

$^1$H NMR (CDCl$_3$, 400 MHz, δ ppm): 1.48 (s, 9H, CH$_3$), 2.10-2.35 (br s, 1H, NH), 2.61-2.84 (m, 2H, CH$_2$), 2.97-3.08 (m, 2H, CH$_2$), 3.08 (s, 3H, CH$_3$), 4.78 (s, 1H, CH), 7.12-7.43 (m, 4H, ArH).

Example 1-5 to a sealed vessel dihydro isoquinoline p-methoxyphenyl formate (1170.2 g, 4 mol), ethanol (7 L) and 10% Pd/c catalyst (60 g) were added, and $H_2$ (3 MPa) was continuously introduced into the vessel after the air in the vessel was replaced with $H_2$, then the reaction mixture was heated to 65° C. and stirred for 24 hours. When analysis indicated the completion of the reaction, the catalyst was recycled by filtering, and the filtrate was concentrated under reduced pressure to get 1131.13 g solid compound of tetrahydroisoquinoline p-methoxyphenyl formate (hereinafter known as compound 3e-5), and the purity of the compound was 93% and the yield was 96%.

The NMR data of the compound 3e-5 was as follows:

$^1$H NMR (CDCl$_3$, 400 MHz, δ ppm): 2.04-2.35 (br s, 1H, NH), 2.66-2.74 (m, 2H, CH$_2$), 2.87-3.02 (m, 2H, CH$_2$), 3.08 (s, 3H, CH$_3$), 4.76 (s, 1H, CH), 7.02-7.13 (m, 4H, ArH), 7.20-7.31 (m, 2H, ArH), 8.16-8.28 (m, 2H, ArH).

Example 1-6 to a sealed vessel dihydro isoquinoline methyl formate (756.8 g, 4 mol), ethanol (7 L) and Raney nickel catalyst (60 g) were added, and $H_2$ (3 MPa) was continuously introduced into the vessel after the air in the vessel was replaced with $H_2$, then the reaction mixture was stirred at 25-30° C. for 10-12 hours. When HPLC analysis indicated the completion of the reaction, the catalyst was recycled by filtering, and the filtrate was concentrated under reduced pressure to get 726.6 g oily compound of tetrahydroisoquinoline methyl formate (compound 3e-1, the purity was 95.5%, and the yield was 95%), and this compound can be directly used in the next step without further purification.

Example 1-7 to a sealed vessel dihydro isoquinoline ethyl formate (812.9 g, 4 mol), ethanol (7 L) and Raney nickel catalyst (60 g) were added, and $H_2$ (3 MPa) was continuously introduced into the vessel after the air in the vessel was replaced with $H_2$, then the reaction mixture was stirred at 25-30° C. for 10-12 hours. When HPLC analysis indicated the completion of the reaction, the catalyst was recycled by filtering, and the filtrate was concentrated under reduced pressure to get 788.2 g oily compound of tetrahydroisoquinoline ethyl formate (compound 3e-2, the purity was 96.8% and the yield was 96%), and this compound can be directly used in the next step without further purification.

Example 1-8 to a sealed vessel dihydro isoquinoline isopropyl formate (869.0 g, 4 mol), ethanol (7 L) and Raney nickel catalyst (60 g) were added, and H$_2$ (3 MPa) was continuously introduced into the vessel after the air in the vessel was replaced with H$_2$, then the reaction mixture was stirred at 25-30° C. for 10-12 hours. When HPLC analysis indicated the completion of the reaction, the catalyst was recycled by filtering, and the filtrate was concentrated under reduced pressure to get 859.9 g oily compound of tetrahydroisoquinoline isopropyl formate (compound 3e-3, the purity was 95.4% and the yield was 98%), and this compound can be directly used in the next step without further purification.

Example 1-9 to a sealed vessel dihydro isoquinoline tertbutyl formate (925.2 g, 4 mol), ethanol (7 L) and Raney nickel catalyst (60 g) were added, and H$_2$ (3 MPa) was continuously introduced into the vessel after the air in the vessel was replaced with H$_2$, then the reaction mixture was stirred at 25-30° C. for 10-12 hours. When HPLC analysis indicated the completion of the reaction, the catalyst was recycled by filtering, and the filtrate was concentrated under reduced pressure to get 895.9 g oily compound of tetrahydroisoquinoline tertbutyl formate (compound 3e-4, the purity was 96.6% and the yield was 96%), and this compound can be directly used in the next step without further purification.

Example 1-10 to a sealed vessel dihydro isoquinoline p-methoxylphenyl formate (1170.2 g, 4 mol), ethanol (7 L) and Raney nickel catalyst (60 g) were added, and H$_2$, (3 MPa) was continuously introduced into the vessel after the air in the vessel was replaced with H$_2$, then the reaction mixture was stirred at 25-30° C. for 10-12 hours. When HPLC analysis indicated the completion of the reaction, the catalyst was recycled by filtering, and the filtrate was concentrated under reduced pressure to get 1131.13 g solid compound of tetrahydroisoquinoline p-methoxylphenyl formate (compound 3e-5, the purity was 95.5% and yield was 95%), and this compound can be directly used in the next step without further purification.

Embodiment 2

Synthesis of Tetrahydroisoquinoline Formamide (a) the reaction route is as follows

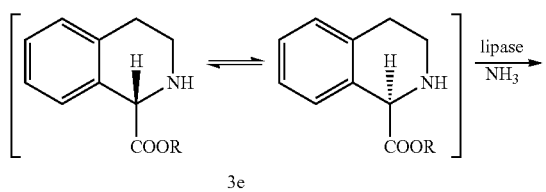

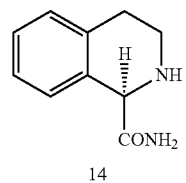

Wherein R represents alkyl, such as methyl, ethyl, isopropyl and tert-butyl.

Example 2-1

To a sealed reactor tetrahydroisoquinoline methyl formate (19.1 mg, 0.1 mmol), 2 mL of 1-hexyl-3-methylimidazolium hexafluorophosphate and 8 mL of tertiary butanol were added, and ammonia gas (340 mg, 20 mmol) or ammonium carbamate (1560 mg, 20 mmol) was added and stirred evenly, subsequently 10 mg of an enzyme was added to start the reaction in water bath at 40° C. in a constant temperature vibrator with HPLC monitoring the reaction. 12 hours later, the monitoring result was listed in the table 2, including the types of the used enzymes, the corresponding conversion and optical purity.

TABLE 2

| | substrate | | | |
| --- | --- | --- | --- | --- |
| | ammonia gas | | ammonium carbamate | |
| enzyme | conversion 12 hours | ee value 12 hours | conversion 12 hours | ee value 12 hours |
| L-AK | 34.0% | 0.8% | 37.2% | 0.9% |
| L-AS | 32.1% | 1.5% | 35.3% | 1.1% |
| L-AY | 36.0% | 0.3% | 33.1% | 0.2% |
| L-PS | 43.2% | 8.1% | 56.4% | 12.6% |
| CALB | 56.4% | 13.3% | 65.6% | 18.1% |
| RML | 35.1% | 3.3% | 35.0% | 3.3% |
| TLL | 37.1% | 3.1% | 33.3% | 3.2% |
| Novo 51032 | 55.2% | 12.0% | 68.5% | 15.3% |
| AULI | 33.1% | 1.4% | 35.7% | 1.4% |

Example 2-2

To a sealed reactor tetrahydroisoquinoline methyl formate (19.1 mg, 0.1 mmol), 2 mL of 1-hexyl-3-methylimidazolium hexafluorophosphate, 8 mL of tertiary butanol and tetrabutyl ammonium hydroxide (2.59 mg, 0.01 mmol) were added, and ammonia gas (340 mg, 20 mmol) or ammonium carbamate (1560 mg, 20 mmol) was added and stirred evenly, subsequently 10 mg of an enzyme was added to start the reaction in water bath at 40° C. in a constant temperature vibrator with HPLC monitoring the reaction. 12 hours later, the monitoring result was listed in the table 3, including: the types of the used enzymes, the corresponding conversion and optical purity.

TABLE 3

| | substrate | | | |
|---|---|---|---|---|
| | ammonia gas + tetrabutyl ammonium hydroxide | | ammonium carbamate + tetrabutyl ammonium hydroxide | |
| enzyme | conversion 12 hours | ee value 12 hours | conversion 12 hours | ee value 12 hours |
| L-AK | 33.1% | 1.6% | 38.0% | 1.8% |
| L-AS | 32.3% | 2.6% | 36.3% | 2.4% |
| L-AY | 35.1% | 3.5% | 38.2% | 3.8% |
| L-PS | 45.2% | 66.3% | 57.3% | 78.5% |
| CALB | 58.5% | 71.2% | 69.1% | 82.2% |
| RML | 38.1% | 3.9% | 42.1% | 5.3% |
| TLL | 42.0% | 8.4% | 43.3% | 8.2% |
| Novo 51032 | 56.6% | 73.8% | 68.8% | 82.1% |
| AULI | 38.3% | 2.1% | 43.1% | 5.4% |

Example 2-3

To a sealed reactor tetrahydroisoquinoline methyl formate (19.1 mg, 0.1 mmol), 2 mL of 1-hexyl-3-methylimidazolium hexafluorophosphate, 8 mL of tertiary butanol and ammonium formate (1266.3 mg, 20 mmol) were added, and triethylamine (2032.5 mg, 20.1 mmol), or imidazole (1380.8 mg, 20.1 mmol), or pyridine (1589.9 mg, 20.1 mmol), or tetrabutyl ammonium hydroxide (5215.3 mg, 20.1 mmol) was added optionally and stirred evenly, and 10 mg of an enzyme was added to start the reaction in water bath at 40° C. in a constant temperature vibrator with HPLC monitoring the reaction. 12 hour later, the monitoring result was listed in the table 4: including the types of the used enzymes, the corresponding conversion and optical purity.

TABLE 4

| | enzyme | | | | | |
|---|---|---|---|---|---|---|
| | L-PS | | CALB | | Novo 51032 | |
| substrate | conversion 12 hours | ee value 12 hours | conversion 12 hours | ee value 12 hours | conversion 12 hours | ee value 12 hours |
| ammonium formate | 5.1% | 0.01% | 8.0% | 0.05% | 7% | 0.04% |
| ammonium formate + triethylamine | 13.3% | 0.9% | 23% | 1.2% | 21.1% | 1.0% |
| ammonium formate + imidazole | 15.2% | 0.8% | 15.2% | 0.8% | 15.2% | 0.7% |
| ammonium formate + pyridine | 13.2% | 0.5% | 13.3% | 0.5% | 13.3% | 0.6% |
| ammonium formate + tetrabutyl ammonium hydroxide | 32.0% | 45.2% | 43.1% | 65.3% | 41.3% | 65.4% |

Example 2-4

To a sealed reactor tetrahydroisoquinoline methyl formate (19.1 mg, 0.1 mmol), 2 mL of 1-hexyl-3-methylimidazolium hexafluorophosphate, 8 mL of tertiary butanol and ammonium acetate (1547.7 mg, 20 mmol) were added, triethylamine (2032.5 mg, 20.1 mmol), or imidazole (1380.8 mg, 20.1 mmol), or pyridine (1589.9 mg, 20.1 mmol), or tetrabutyl ammonium hydroxide (5215.3 mg, 20.1 mmol) was optionally added and stirred evenly, and 10 mg of an enzyme was added to start the reaction in water bath at 40° C. in a constant temperature vibrator with HPLC monitoring the reaction. 12 hours later, the monitoring result was listed in the table 5, including the types of the used enzymes, the corresponding conversion and optical purity.

TABLE 5

| | enzyme | | | | | |
|---|---|---|---|---|---|---|
| | L-PS | | CALB | | Novo 51032 | |
| substrate | conversion 12 hours | ee value 12 hours | conversion 12 hours | ee value 12 hours | conversion 12 hours | ee value 12 hours |
| ammonium acetate | 3.2% | 0.01% | 5.1% | 0.02% | 6.4% | 0.01% |
| ammonium acetate + triethylamine | 10.2% | 0.1% | 22.1% | 1.2% | 21.5% | 1.1% |
| ammonium acetate + imidazole | 14.1% | 0.8% | 18.1% | 0.9% | 19.6% | 2.2% |
| ammonium acetate + pyridine | 12.2% | 0.2% | 14.2% | 0.6% | 16.1% | 0.5% |

TABLE 5-continued

| | enzyme | | | | | |
| --- | --- | --- | --- | --- | --- | --- |
| | L-PS | | CALB | | Novo 51032 | |
| substrate | conversion 12 hours | ee value 12 hours | conversion 12 hours | ee value 12 hours | conversion 12 hours | ee value 12 hours |
| ammonium acetate + tetrabutyl ammonium hydroxide | 33.4% | 44.5% | 45.2% | 64.2% | 43.1% | 62.1% |

Example 2-5

To a sealed reactor tetrahydroisoquinoline methyl formate (19.1 mg, 0.1 mmol), 2 mL of 1-hexyl-3-methylimidazolium hexafluorophosphate, 8 mL of tertiary butanol, and ammonium chloride (1075.4 mg, 20 mmol) were added, and triethylamine (2032.5 mg, 20.1 mmol), or imidazole (1380.8 mg, 20.1 mmol), or pyridine (1589.9 mg, 20.1 mmol), or tetrabutyl ammonium hydroxide (5215.3 mg, 20.1 mmol) was optionally added and stirred evenly, and 10 mg of enzyme was added to start the reaction in water bath at 40° C. in a constant temperature vibrator with HPLC monitoring the reaction. 12 hours later, the monitoring result was listed in the table 6, including the types of the used enzymes, the corresponding conversion and optical purity.

TABLE 6

| | enzyme | | | | | |
| --- | --- | --- | --- | --- | --- | --- |
| | L-PS | | CALB | | Novo 51032 | |
| substrate | conversion 12 hours | ee value 12 hours | conversion 12 hours | ee value 12 hours | conversion 12 hours | ee value 12 hours |
| ammonium chloride | 3.% | 0.01% | 6.1% | 0.02% | 4.0% | 0.01% |
| ammonuim chloride + triethylamine | 16.1% | 0.9% | 28.2% | 1.0% | 25.0% | 8.2% |
| ammonium chloride + imidazole | 17.1% | 0.2% | 23.3% | 1.1% | 23.1% | 1.8% |
| ammonium chloride + pyridine | 13.2% | 0.8% | 24.4% | 0.8% | 21.1% | 0.8% |
| ammonium chloride + tetrabutyl ammonium hydroxide | 35.2% | 32.1% | 48.5% | 68.4% | 47.2% | 69.0% |

Example 2-6

Experiments for Solvents

To a sealed reactor tetrahydroisoquinoline methyl formate (19.1 mg, 0.1 mmol), 1-hexyl-3-methylimidazolium hexafluorophosphate (2 mL), and 8 mL of diisopropyl ether ester (8 mL), or dioxane (8 mL), or tetrahydrofuran (8 mL), or isopropanol (8 mL), or methyl tert-butyl ether (8 mL) were added, and tetrabutyl ammonium hydroxide (2.59 mg, 0.01 mmol) and ammonium carbamate (1560 mg, 20 mmol) were added and stirred evenly, subsequently 10 mg of an enzyme was added to start the reaction in water bath in a constant temperature vibrator at 3° C., 10° C., 25° C., 50° C. respectively, with HPLC monitoring the reaction. 12 hours later, the monitoring result was listed in the table 7, including the types of the used enzymes, the corresponding conversion and optical purity.

TABLE 7

| | enzyme | | | | | |
| --- | --- | --- | --- | --- | --- | --- |
| | L-PS | | CALB | | Novo 51032 | |
| solvent | conversion 12 hours | ee value 12 hours | conversion 12 hours | ee value 12 hours | conversion 12 hours | ee value 12 hours |
| diisopropyl ether ester | 33.3% | 56.3% | 45.5% | 63.4% | 46.1% | 65.1% |
| dioxane | 40.5% | 61.5% | 55.5% | 63.5% | 57.2% | 66.3% |
| tetrahydrofuran | 43.1% | 51.2% | 53.3% | 60.2% | 53.8% | 61.1% |
| isopropanol | 51.0% | 66.5% | 61.5% | 72.4% | 63.3% | 73.5% |
| methyl tertiary butyl ether | 40.3% | 43.7% | 44.5% | 63.3% | 43.2% | 63.3% |

Example 2-7

Experiments for Reaction Temperature

To a sealed reactor tetrahydroisoquinoline methyl formate (19.1 mg, 0.1 mmol), 1-hexyl-3-methylimidazolium hexafluorophosphate (2 mL), tertiary butanol (8 mL) and tetrabutyl ammonium hydroxide (2.59 mg, 0.01 mmol) were added, and ammonium carbamate (1560 mg, 20 mmol) was added and stirred evenly; subsequently 10 mg of an enzyme was added to start the reaction in water bath in a constant temperature vibrator at 3° C., 10° C., 25° C., 50° C. respectively, with HPLC monitoring the reaction. 12 hours later, the monitoring result was listed in the table 8, including the types of the used enzymes, the corresponding conversion and optical purity.

TABLE 8

| | enzyme | | | | | |
|---|---|---|---|---|---|---|
| | L-PS | | CALB | | Novo 51032 | |
| temperature | conversion 12 hours | ee value 12 hours | conversion 12 hours | ee value 12 hours | conversion 12 hours | ee value 12 hours |
| 3° C. | 12.1% | 36.1% | 23.4% | 42.3% | 24.2% | 48.1% |
| 20° C. | 31.4% | 68.3% | 43.8% | 71.1% | 40.1% | 72.2% |
| 30° C. | 45.4% | 79.4% | 58.6% | 85.2% | 56.1% | 89.1% |
| 50° C. | 55.1% | 63.2% | 55.4% | 55.0% | 55.0% | 55.3% |

Example 2-8

Experiments for Substrates

To a sealed reactor racemic tetrahydroisoquinoline methyl formate (19.1 mg, 0.1 mmol), or ethyl formate (20.5 mg, 0.1 mmol), or isopropyl formate (21.98 mg, 0.1 mmol), or tert-butyl formate (23.33 mg, 0.1 mmol), 2 ml of 1-hexyl-3-methylimidazolium hexafluorophosphate, 8 mL of tertiary butanol, and tetrabutyl ammonium hydroxide (2.59 mg, 0.01 mmol) were added, and ammonium carbamate (1560 mg, 20 mmol) was added and stirred evenly; subsequently 10 mg of an enzyme was added to start the reaction in water bath at 40° C. in a constant temperature vibrator, with HPLC monitoring the reaction. 24 hours later, the monitoring result was listed in the table 9, including the types of the used enzymes, the corresponding conversion and optical purity.

TABLE 9

| | enzymes | | | | | |
|---|---|---|---|---|---|---|
| | L-PS | | CALB | | Novo 51032 | |
| substrates | conversion 24 hours | ee value 24 hours | conversion 24 hours | ee value 24 hours | conversion 24 hours | ee value 24 hours |
| tetrahydroisoquinoline methyl formate | 99.5% | 91.3% | 99.4% | 96.3% | 99.5% | 96.5% |
| tetrahydroisoquinoline ethyl formate | 99.3% | 93.5% | 99.3% | 97.5% | 99.3% | 97.5% |
| tetrahydroisoquinoline isopropyl formate | 99.3% | 93.5% | 99.5% | 98.5% | 99.3% | 98.5% |
| tetrahydroisoquinoline tert-butyl formate | 99.2% | 95.7% | 99.5% | 98.3% | 99.6% | 98.4% |

Example 2-9

Preparation of the Compound 14

To a sealed reactor tetrahydroisoquinoline methyl formate (191.3 g, 1 mol), 0.5 L of 1-hexyl-3-methylimidazolium hexafluorophosphate, 2 L of tertiary butanol and tetrabutyl ammonium hydroxide (25.9 g, 0.1 mol) were added and stirred evenly, and ammonium carbamate (117 g, 1.5 mol) was added and stirred evenly, subsequently 10 g of an enzyme (Novo 51032) was added to start the reaction under stirring in water bath at 40° C. in a constant temperature stirrer, with HPLC monitoring the reaction. 24 hours later, the conversion was 99.6% and the reaction was ended, the enzyme was recycled by filtering and returned to the reactor. In repeated batch reactions, to the reactor tetrahydroisoquinoline methyl formate (191.3 g, 1 mol), 0.5 L of 1-hexyl-3-methylimidazolium hexafluorophosphate. 2 L of tertiary butanol and tetrabutyl ammonium hydroxide (25.9 g, 0.1 mol) were added respectively and stirred evenly, and ammonium carbamate (117 g, 1.5 mol) was added to perform the next batch reaction, the reaction was repeated continuously for 5 times, and the conversion of each batch is more than 99%.

The post treatment for single batch reaction: 3 M hydrochloric acid (1 L) was dropwise added to the reaction mixture liquid under stirring and the temperature was kept at 20-25° C. during addition. When the addition was completed, the 1-hexyl-3-methylimidazolium hexafluorophosphate and tertiary butanol were in the upper layer and the product and other components were in the lower layer of water phase after standing and layering of the solution.

(1) The processing method for the organic layer: the upper layer of 1-hexyl-3-methylimidazolium hexafluorophosphate and tertiary butanol was separated and washed with saturated sodium bicarbonate (100 mL) and saturated salt water (2×50 mL) respectively. The washing liquid was incorporated into the lower layer of water phase. The organic phase was dried over anhydrous sodium sulfate and distilled to recycle tertiary butanol, and the residual 1-hexyl-3-methylimidazolium hexafluorophosphate was recycled for use in a next batch reaction.

(2) The processing method for the water layer: the water phase was neutralized with saturated sodium bicarbonate to neutrality, then the resulting solution was extracted with ethyl acetate (3×200 mL), dried by anhydrous sodium sulfate and concentrated to get the residue. Finally, the residue was recrystallized by 95% ethanol (1000 mL) to get 146.2 g white solid of compound 14, wherein the separation yield was 83% and ee value was 99.3%.

The NMR data of compound 14 was as follows:
$^1$H NMR(CDCl$_3$, 400 MHz, δ ppm): 2.03 (brs, 1H), 2.63-2.70 (m, 1H), 2.74-2.81 (m, 1H), 2.98 (t, J=5.9 Hz, 2H), 4.34 (s, 1H), 6.97 (brs, 2H), 7.00-7.02 (m, 1H), 7.09-7.11 (m, 2H), 7.40-7.44 (m, 1H).

MS (ESI, +ve): m/z: 177.1 [M+H]$^+$.

Example 2-10

Preparation of the Compound 14

To a sealed reactor tetrahydroisoquinoline tertbutyl formate (233.3 g, 1 mol), 0.5 L of 1-hexyl-3-methylimidazolium hexafluorophosphate, 2 L of tertiary butanol and tetrabutyl ammonium hydroxide (12.95 g, 0.05 mol) were added and stirred evenly, and ammonium carbamate (117 g, 1.5 mol) was added and stirred evenly, subsequently 10 g of an enzyme (Novo 51032) was added to start the reaction under stirring in water bath at 40° C. in a constant stirrer, with HPLC monitoring the reaction. 24 hours later, the conversion is 99.7%, and the reaction was ended. Finally, the enzyme was recycled by filtering and returned to the reactor. In repeated batch reactions, to the reactor tetrahydroisoquinoline methyl formate (233.3 g, 1 mol), 0.5 L of 1-hexyl-3-methylimidazolium hexafluorophosphate, 2 L of tertiary butanol and tetrabutyl ammonium hydroxide (12.95 g, 0.05 mol) were respectively added and stirred evenly; and ammonium carbamate (117 g, 1.5 mol) was added to perform a next batch reaction, the reaction was repeated continuously for 5 times, and the conversion of each batch was more than 99%.

The post treatment for single batch reaction: 3M hydrochloric acid (1 L) was dropwise added to the reaction mixture liquid under stirring and the temperature was kept at 20-25° C. during addition. When the addition was completed, the 1-hexyl-3-methylimidazolium hexafluorophosphate and tertiary butanol were in the upper layer and the product and other components were in the lower layer of water phase after standing and layering of the solution.

(1) The processing method for the organic layer: the upper layer of 1-hexyl-3-methylimidazolium hexafluorophosphate and tertiary butanol was separated and washed with saturated sodium bicarbonate (100 mL) and saturated salt water (2×50 mL) respectively. The washing liquid was incorporated into the lower layer of water phase. The organic phase was dried over anhydrous sodium sulfate and distilled to recycle tertiary butanol, and the residual 1-hexyl-3-methylimidazolium hexafluorophosphate was recycled for use in a next batch reaction.

(2) The processing method for the water layer: the water phase was neutralized with saturated sodium bicarbonate to neutrality, then the resulting solution was extracted with ethyl acetate (3×200 ml), dried by anhydrous sodium sulfate and concentrated to get the residue. Finally, the residue was recrystallized by 95% ethanol (1000 mL) to get 163.9 g white solid of compound 14, wherein the separation yield was 93% and ee value was 99.2%, and the melt point was 178-180° C.

The NMR data of compound 14 was as follows:
$^1$H NMR (CDCl$_3$, 400 MHz, δ ppm): 2.03 (brs, 1H), 2.63-2.70 (m, 1H), 2.74-2.81 (m, 1H), 2.98 (t, J=5.9 Hz, 2H), 4.34 (s, 1H), 6.97 (brs, 2H), 7.00-7.02 (m, 1H), 7.09-7.11 (m, 2H), 7.40-7.44 (m, 1H).

MS (ESI, +ve): m/z: 177.1 [M+H]$^+$.

Example 3

Synthesis of the Compound 16 Using the Following Reaction Scheme

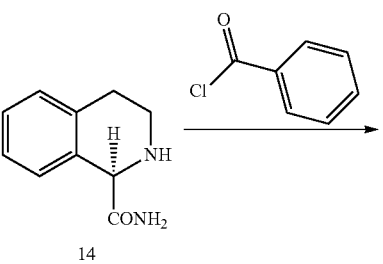

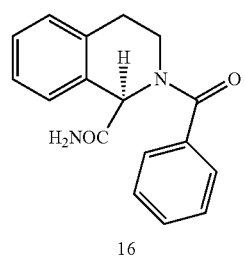

To a reactor the compound 14 (4.4 g, 25 mmol, 1.1 eq), triethylamine (3.78 g, 5.22 mL, 37.5 mmol, 1.5 eq), and dichloromethane (124 mL) were added and cooled to 0° C. in ice bath. Benzoyl chloride (3.86 g, 27.47 mmol, 1.1 eq) was added dropwise to the mixture under stirring, and the temperature was kept at 0° C. during addition. When the addition was completed, the reaction mixture was stirred at 20-25° C. for 6-8 hours. When HPLC analysis indicated the completion of the reaction, the reaction was quenched with water (16 L) and the mixture was stirred for further 30 mins. The organic layer was separated, and washed with saturated sodium bicarbonate, 0.5N HCl and salt water respectively, dried over anhydrous sodium sulfate, and concentrated under reduced pressure to get the residue. Finally, the residue was recrystallized with ethanol to get the compound 16 (6.59 g, yield was 96%, the purity was 99% and ee value was 99.2%).

The NMR data of the compound 16 was as follows:
$^1$H NMR (CDCl$_3$, 400 MHz, δ ppm): 2.97-3.09 (m, 2H), 3.89-4.02 (m, 2H), 5.95 (s, 1H), 7.08 (brs, 2H), 7.40-7.51 (m, 3H), 7.56-7.64 (m, 2H), 7.78-7.98 (m, 4H).

MS (ESI, +ve): m/z: 281.1 [M+H]$^+$.

Example 4

Synthesis of the Compound 17 Using the Following Reaction Scheme

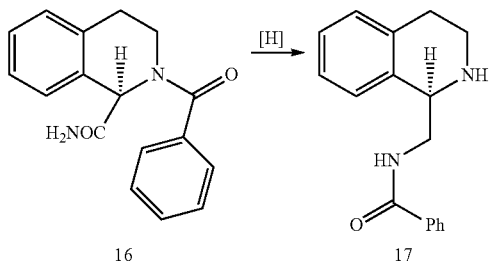

To a sealed reactor the compound 16 (5.6 g, 20 mmol), anhydrous methanol (200 mL) and 5% ruthenium catalyst Ru/C (0.5 g) were added, and $H_2$ (3 MPa) was continuously introduced to the reactor after the air in the reactor was replaced with $H_2$. The mixture was heated to 90-95° C. and stirred for 16-18 hours. When the analysis indicated the completion of the reaction, the catalyst was recycled by filtering. The filtrate was concentrated under reduced pressure and the residue was recrystallized with the mixed solvent of ethanol and n-hexane in a volume ratio of 1:3 to get 4.58 g light yellow solid of compound 17, wherein the yield is 86%, melt point is 125-127° C. and ee value is more than 99%.

The NMR data of the compound 17 was as follows:

$^1$H NMR (CDCl$_3$, 400 MHz, δ ppm): 2.68-2.76 (m, 1H), 2.88-3.01 (m, 3H), 3.17-3.47 (m, 1H), 3.89-4.21 (m, 1H), 4.90-5.15 (m, 1H), 6.91-7.17 (m, 2H), 7.56-7.64 (m, 3H), 7.72-8.01 (m, 4H).

MS (ESI, +ve): m/z: 267.1 [M+H]$^+$

Example 5

Synthesis of Compound 19

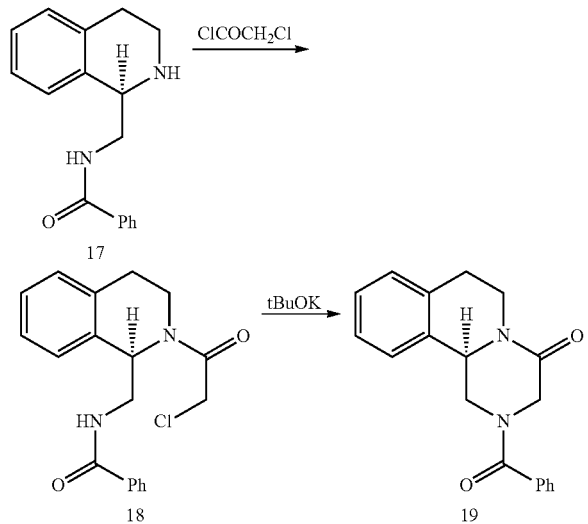

Example 5-1 to a reactor the compound 17 (2.7 g, 10 mmol), toluene (30 mL) and 50% sodium hydroxide solution (1.84 g, 23 mmol) were added and stirred evenly, and chloroacetyl chloride (1.4 g, 12 mmol) was added dropwise, then after the addition the reaction mixture was stirred at room temperature for 3 hours. When HPLC analysis indicated the completion of the reaction, benzyl triethyl ammonium chloride (22.7 mg, 0.1 mmol) was added and the resulting mixture was heated to 80° C. and the reaction was performed for 1-2 hours until HPLC analysis indicating the completion of the reaction. The insoluble substance was filtered out and the toluene layer was washed with water and saturated salt water in sequence, dried over anhydrous magnesium sulfate, and concentrated under reduced pressure to get the crude product, finally the crude product was recrystallized with anhydrous ethanol to get 2.73 g pure solid of (R)-benzoyl praziquantel, i.e., the compound 19, wherein the yield of the compound 19 was 89%, the melt point was 128-130° C. and ee value was more than 99%.

The NMR data of the compound 19 was as follows:

$^1$H NMR (CDCl$_3$, 400 MHz, δ ppm): 2.49-2.53 (m, 1H, CH$_2$), 2.74-2.70 (m, 1H, CH$_2$), 2.88-2.78 (m, 2H, CH$_2$), 3.26 (d, 1H, CH$_2$), 4.21 (d, 1H, CH$_2$), 4.37 (dd, 1H, CH$_2$), 4.82-4.76 (m, 1H, CH$_2$), 4.97 (dd, 1H, CH), 7.12 (d, 2H, Ar—H), 7.26-7.19 (m, 3H, Ar—H), 7.32 (d, 2H, Ar—H), 7.68 (d, 2H, Ar—H).

MS (ESI, +ve): m/z: 307.1 [M+H]$^+$.

Example 5-2 to a reactor the compound 17 (2.7 g, 10 mmol), ethyl acetate (30 mL) and Potassium tert-butoxide (2.58 g, 23 mmol) were added and stirred evenly, and chloroacetyl chloride (1.4 g, 12 mmol) was added dropwise, then after the addition the reaction mixture was stirred at room temperature for 3 hours. When HPLC analysis indicated the completion of the reaction, benzyl triethyl ammonium chloride (22.7 mg, 0.1 mmol) was added and the resulting mixture was heated to reflux and the reaction was performed for 4-5 hours until HPLC analysis indicating the completion of the reaction. The insoluble substance was filtered out and the ethyl acetate layer was washed with water and saturated salt water in sequence, dried over anhydrous magnesium sulfate, and concentrated under reduced pressure to get the crude product, finally the crude product was recrystallized with anhydrous ethanol to get 2.39 g pure solid of (R)-benzoyl praziquantel, i.e., the compound 19, wherein the yield of the compound 19 was 78%, the melt point was 128-130° C. and ee value was more than 99%.

The NMR data of the compound 19 was as follows:

$^1$H NMR (CDCl$_3$, 400 MHz, δ ppm): 2.49-2.53 (m, 1H, CH$_2$), 2.74-2.70 (m, 1H, CH$_2$), 2.88-2.78 (m, 2H, CH$_2$), 3.26 (d, 1H, CH$_2$), 4.21 (d, 1H, CH$_2$), 4.37 (dd, 1H, CH$_2$), 4.82-4.76 (m, 1H, CH$_2$), 4.97 (dd, 1H, CH), 7.12 (d, 2H, Ar—H), 7.26-7.19 (m, 3H, Ar—H), 7.32 (d, 2H, Ar—H), 7.68 (d, 2H, Ar—H).

MS (ESI, +ve): m/z: 307.1 [M+H]$^+$.

Example 5-3 to a reactor the compound 17 (5.4 g, 20 mmol), dichloromethane (50 mL) and anhydrous potassium carbonate (6.5 g, 46 mmol) were added and stirred evenly, and chloroacetyl chloride (2.8 g, 24 mmol) was added dropwise, then after the addition the reaction mixture heated to 40-45° C. and stirred for 5-6 hours. When HPLC analysis indicated the completion of the reaction, benzyl triethyl ammonium chloride (45.4 mg, 0.2 mmol) was added and the resulting mixture was heated to reflux and the reaction was performed for 10-12 hours until HPLC analysis indicating the completion of the reaction. The insoluble substance was filtered out and the dichloromethane layer was washed with water and saturated salt water in sequence, dried over anhydrous magnesium sulfate, and concentrated under reduced pressure to get the crude product, finally the crude product was recrystallized with anhydrous ethanol to get 4.9 g pure solid of (R)-benzoyl praziquantel, i.e., the compound 19, wherein the yield of the compound 19 was 80%, the melt point was 128-130° C. and ee value was more than 99%.

The NMR data of the compound 19 was as follows:

$^1$H NMR (CDCl$_3$, 400 MHz, δ ppm): 2.49-2.53 (m, 1H, CH$_2$), 2.74-2.70 (m, 1H, CH$_2$), 2.88-2.78 (m, 2H, CH$_2$), 3.26 (d, 1H, CH$_2$), 4.21 (d, 1H, CH$_2$), 4.37 (dd, 1H, CH$_2$), 4.82-4.76 (m, 1H, CH$_2$), 4.97 (dd, 1H, CH), 7.12 (d, 2H, Ar—H), 7.26-7.19 (m, 3H, Ar—H), 7.32 (d, 2H, Ar—H), 7.68 (d, 2H, Ar—H).

MS (ESI, +ve): m/z: 307.1 [M+H]$^+$.

Example 6

Synthesis of (R)-praziquantel (Compound 12)

(a) the synthesis route is as follows:

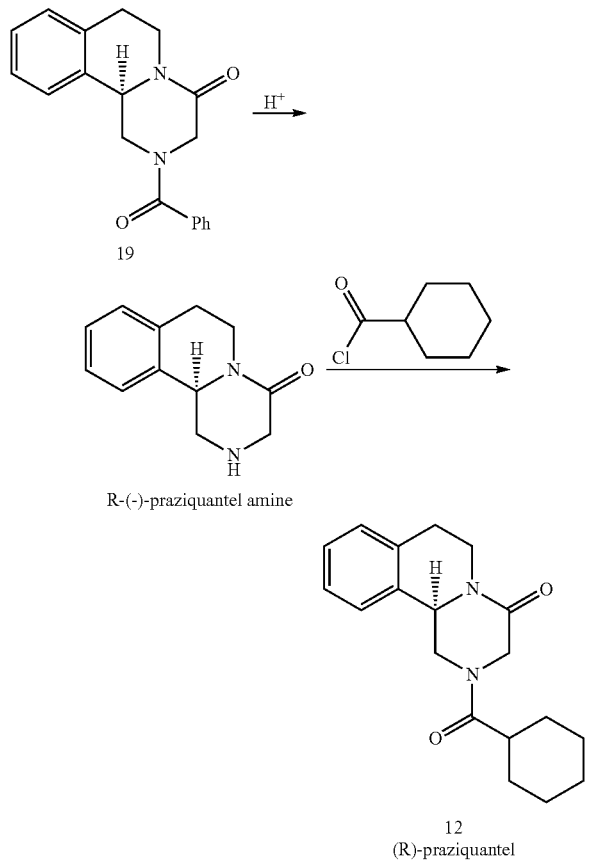

Example 6-1

Synthesis of the intermediate R-(−)-praziquantel amine (R-(−)-PZQA)

To a reactor, the compound 19 (15.32 g, 50 mmol, 1 eq.), phosphoric acid (80 mL) were added and stirred at 120° C. for 3 hours. When HPLC indicated the completion of the reaction, the mixture was cooled to 0° C. and poured into crushed ice water (300 mL) and adjusted pH=12 with 10% sodium hydroxide. The water layer was extracted with dichloromethane (3×5 mL). The organic layers were incorporated together and dried, concentrated to get the crude product, and the crude product was recrystallized with toluene to get 8.9 g light yellow solid of the intermediate R-(−)-PZQA, wherein the yield of the intermediate was 88.1%, the melt point is 122-123° C. and ee value was 99.1%.

The NMR data of the intermediate R-(−)-praziquantel amine:

$^1$H NMR (CDCl$_3$, 400 MHz, δ ppm): 1.76 (bs, 1H), 2.64-3.02 (m, 4H), 3.49 (d, J=17.6, 1H), 3.61 (d, 1H), 3.67 (ddd, 1H), 4.69-4.85 (m, 2H), 7.04-7.20 (m, 4H).

MS (ESI, +ve): m/z: 203.1 [M+H]$^+$.

Example 6-2

Synthesis of the intermediate R-(−)-praziquantel amine (R-(−)-PZQA)

To a reactor, the compound 19 (15.32 g, 50 mmol, 1 eq.), ethanol (130 mL) and hydrochloric acid (1 M, 600 mL) were added and heated to reflux and stirred for 28-30 hours. When HPLC indicated the completion of the reaction, the mixture was cooled to 0° C. and extracted with ethyl acetate (3×50 mL) and adjusted pH=12 with 10% sodium hydroxide. The water layer was extracted with dichloromethane (3×50 mL). The organic layers were incorporated together and washed with salt water, dried with anhydrous sodium sulfate, and concentrated to get the crude product, and the crude product was recrystallized with toluene to get 9.4 g light yellow solid of the intermediate R-(−)-PZQA, wherein the yield of the intermediate was 93%, the melt point is 122-123° C. and ee value was 99.4%.

The NMR data of the intermediate R-(−)-praziquantel amine:

$^1$H NMR (CDCl$_3$, 400 MHz, δ ppm): 1.76 (bs, 1H), 2.64-3.02 (m, 4H), 3.49 (d, J=17.6, 1H), 3.61 (d, 1H), 3.67 (ddd, 1H), 4.69-4.85 (m, 2H), 7.04-7.20 (m, 4H).

MS (ESI, +ve): m/z: 203.1 [M+H]$^+$.

Example 6-3

Synthesis of (R)-praziquantel

To a reactor the intermediate R-(−)-praziquantel amine (5.05 g, 25 mmol, 1 eq.), triethylamine (3.78 g, 5.22 mL, 37.5 mmol, 1.5 eq.) and dichloromethane (124 mL) were added and cooled in ice bath to 0° C. Cyclohexanecarboxylic acid chloride (4.05 g, 3.69 mL, 27.47 mmol, 1.1 eq.) was added dropwise to the mixture under stirring and the temperature was kept at 0° C. during addition. After the addition, the resulting mixture was stirred at 20-25° C. for 16 hours. When HPLC analysis indicated the completion of the reaction, the reaction was quenched with water (16 mL), and the solution was stirred for further 30 mins. The organic layer was separated and washed with saturated sodium carbonate, 0.5 N HCl and salt water, dried over anhydrous sodium sulfate and concentrated to get the residue. The residue was recrystallized with the mixed solvent of acetone/n-hexane (55 mL, 1/1, v/v) to get 7.42 g colorless crystal of (R)-praziquantel, wherein the yield of (R)-praziquantel was 95%, the purity was 99.2% and the melt point was 113-115° C.

The NMR data of (R)-praziquantel was as follows:

$^1$H NMR (DMSO-d$_6$, 400 MHz, δ ppm): 1.21-1.96 (m, 10H, 5×CH$_2$), 2.45-2.50 (m, 1H, CH), 2.78-3.05 (m, 4H, CH$_2$), 4.10 (d, 1H, CH$_2$), 4.48 (d, 1H, CH$_2$), 4.79-4.85 (m, 2H, CH$_2$), 5.20 (d, 1H, CH), 7.12-7.30 (m, 4H, Ar—H).

MS (ESI, +ve): m/z: 313.1 [M+H]$^+$.

The above embodiments are given for illustrating the technical concept or features of the invention, and this is intended to enable a person skilled in the art to appreciate the content of the invention and further implement it, and the protecting scope of the invention can not be limited hereby. Also, any equivalent variations or modifications made according to the spirit of the invention should be covered within the protecting scope of the invention.

What is claimed is:

1. A method for preparing (R)-praziquantel, comprising the following reaction scheme:

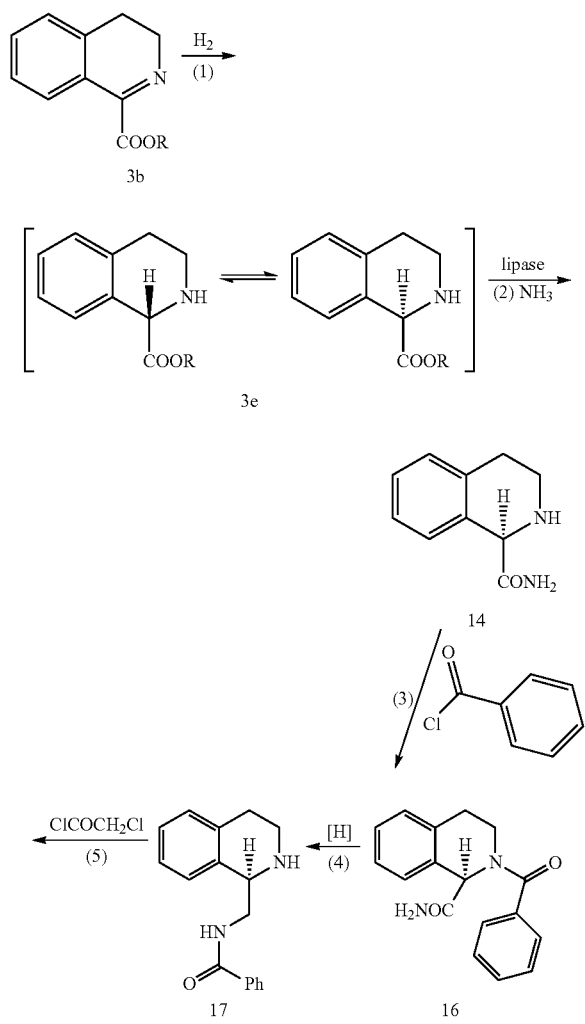

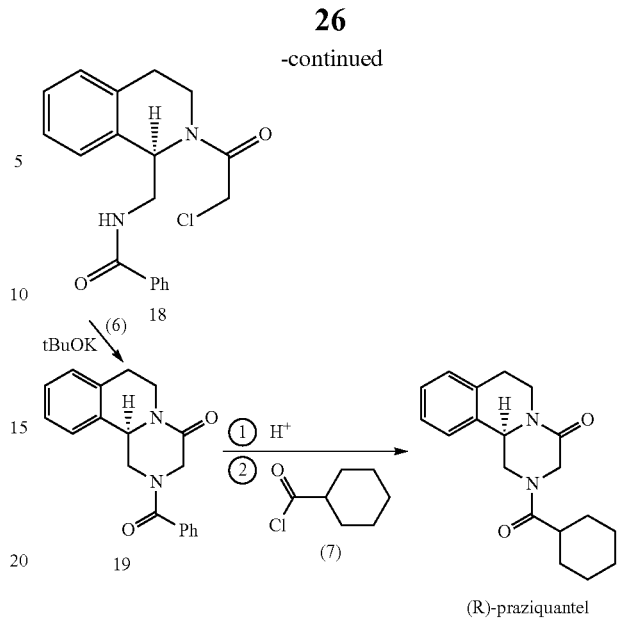

wherein
R represents alkyl; and
wherein the lipase stereo-selectively ammonolyzes a (R)-tetrahydroisoquinoline formate of the racemic compound 3e to obtain a pure optical (R)-tetrahydroisoquinoline formamide having the structure of compound 14.

2. The method for preparing (R)-praziquantel as claimed in claim 1, wherein R is selected from the group consisting of methyl, ethyl, isopropyl and tert-butyl.

3. The method for preparing (R)-praziquantel as claimed in claim 1, wherein the lipase is selected from one or more microbial lipases derived from the group consisting of *Aspergillus niger*, *Candida rugosa*, *Candida cylindracea*, *Rhizomucor miehei*, *Candida Antarctica*, *Pseudomonas cepacia*, *Pseudomonas fluorescens*, *Thermomyces lanuginose*, *Bacillus subtilis*, *Fusarium solani pisi*, *Alcaligenes* sp, *Rhizopus niveus*, *Mucor javanicus* and *Rhizopus oryzae*, and the lipases derived from *Thermomyces lanuginose*, *Fusarium solani pisi*, *Bacillus subtilis*, *Pseudomonas cepacia* and *Pseudomonas fluorescens*.

4. The method for preparing (R)-praziquantel as claimed in claim 1, wherein the step (2) comprises:
adding the racemic compound 3e, an ionic liquid, a solvent and an optional organic base to a sealed reactor, and adding an ammonia source and stirring evenly;
adding a lipase to start the reaction in a constant temperature vibrator with HPLC monitoring the reaction: ending the reaction when the conversion is more than 99%, and filtering the reaction solution to recycle the lipase such that the lipase can be used in a next batch reaction, and the filtrate is post-processed to get the (R)-praziquantel.

5. The method for preparing (R)-praziquantel as claimed in claim 4, wherein the solvent is selected from the group consisting of tertiary butanol, diisopropyl ether ester, dioxane, tetrahydrofuran, isopropanol, methyl tert-butyl ether and any combination thereof.

6. The method for preparing (R)-praziquantel as claimed in claim 4, wherein the ionic liquid is selected from the group consisting of 1-n-butyl-3-methylimidazolium tetrafluoroborate, 1-n-butyl-3-methylimidazolium hexafluorophosphate, 1-n-butyl-3-methylimidazolium bis[(trifluoromethyl)sulfonyl]imide and 1-n-butyl-pyridinium hexafluorophosphate.

7. The method for preparing (R)-praziquantel as claimed in claim 4, wherein the ammonia source is selected from one or more of ammonia gas, ammonium carbamate, ammonium formate, ammonia acetate and ammonia chloride.

8. The method for preparing (R)-praziquantel as claimed in claim 4, wherein the reaction is performed in the presence of an organic base selected from the group consisting of triethylamine, imidazole, pyridine, tetrabutyl ammonium hydroxide and any combination thereof.

9. The method for preparing (R)-praziquantel as claimed in claim 4, wherein the reaction temperature is 20-50° C.

10. The method for preparing (R)-praziquantel as claimed in claim 1, wherein the step (1) comprises:
    reacting the compound 3b with $H_2$ at 60-70° C. in the presence of a Pd/C catalyst; and
    after the completion of the reaction, filtering the reaction solution to recycle the catalyst and concentrating the filtrate under reduced pressure to get the racemic compound 3e.

11. The method for preparing (R)-praziquantel as claimed in claim 1, wherein the step (3) comprises:
    adding the compound 14, triethylamine and dichloromethane to a reactor;
    cooling the mixture to 0-2° C. in ice bath;
    adding dropwise benzoyl chloride at 0-2° C.;
    after the addition, stirring the reaction mixture at 20-25° C. for 6-8 hours with HPLC monitoring the reaction;
    subsequently after the completion of the reaction, quenching the reaction with water and stirring the solution for further 30-40 mins; and
    separating, washing, drying and concentrating under reduced pressure the organic phase layer, and recrystallizing the residue with ethanol to get the compound 16.

12. The method for preparing (R)-praziquantel as claimed in claim 1, wherein the step (4) comprises:
    adding the compound 16, an anhydrous methanol and a ruthenium catalyst Ru/C to a scaled reactor, and replacing the air in the reactor with $H_2$ and further continuously introducing $H_2$;
    heating the mixture to 90-95° C. and stirring for 16-18 hours until the analysis indicating the completion of the reaction;
    filtering the reaction solution to recycle the catalyst and concentrating the filtrate under reduced pressure; and
    recrystallizing the residue with the mixed solvent of ethanol and n-hexane in a volume ratio of 1:2-4 to get light yellow solid of compound 17.

13. The method for preparing (R)-praziquantel as claimed in claim 1, wherein the step (5) comprises:
    adding the compound 17, an organic solvent and a solution of a base to a reactor and stirring evenly and adding dropwise chloroacetylchloride; and
    stirring the mixture at room temperature for 3-4 hours until HPLC analysis indicating the completion of the reaction, wherein the resulting reaction mixture can be used directly in the next reaction.

14. The method for preparing (R)-praziquantel as claimed in claim 1, wherein the step (6) comprises:
    adding benzyl-triethyl ammonium chloride to the reaction mixture of step (5) and heating the mixture to 75-85° C. to perform the reaction for 1-2 hours until HPLC analysis indicating the completion of the reaction;
    filtering out the insoluble, and washing, drying and concentrating under reduced pressure the layer of organic solvent to get the crude product; and
    recrystallizing the crude product with anhydrous ethanol to get compound 19.

15. The method for preparing (R)-praziquantel as claimed in claim 1, wherein the step (7) further comprising the steps of:
    a. preparing the intermediate R-(−)-praziquantel amine from compound 19 in the presence of phosphoric acid or hydrochloric acid; and

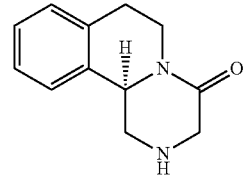

R-(−)-praziquantel amine
    b. reacting the intermediate R-(−)-praziquantel amine with cyclohexane formyl chloride in a solvent in the presence of triethylamine at 20-25° C. to get the (R)-praziquantel.

* * * * *